United States Patent
Cappola

[11] Patent Number: 6,036,126
[45] Date of Patent: Mar. 14, 2000

[54] APPARATUS FOR SEPARATING PARTICLES OF COHESIVE MATERIAL ACCORDING TO SIZE AND PROCESS

[75] Inventor: Michael L. Cappola, Wilton, Conn.

[73] Assignee: Boehringer Ingelheim Pharmaceuticals, Inc., Ridgefield, Conn.

[21] Appl. No.: 09/208,393

[22] Filed: Dec. 9, 1998

[51] Int. Cl.[7] .................................................. B02C 19/00
[52] U.S. Cl. ..................... 241/69; 209/315; 209/320; 209/351; 241/84.1; 241/175
[58] Field of Search ................................. 209/309, 315, 209/320, 350, 351; 241/175, 69, 84.1, 85, 89.4, 92, 94

[56] References Cited

U.S. PATENT DOCUMENTS 1,293,188  2/1919  Peersch ..................................... 241/175
3,762,656  10/1973  Deve ........................................ 241/84.1

FOREIGN PATENT DOCUMENTS 1283676  12/1961  France ..................................... 241/175

*Primary Examiner*—Mark Rosenbaum
*Attorney, Agent, or Firm*—R. P. Raymond; M-E. M. Devlin; A. Stempel

[57] ABSTRACT

Milling/sizing apparatus which includes individual and/or nested sieves each of which may also include a quantity of beads, disks and/or other geometric or non-geometric shapes. The sieves can be rotated, vibrated or agitated in any and all combinations by various methods to achieve independently horizontal rotation and vertical reciprocation (similar to a merry-go-round) to efficiently segregate, size or mill cohesive and polydisperse powder particles to specific size ranges. The invention also contemplates a method for using the apparatus in the sizing and quantification of aggregated particles of cohesive disperse powders.

4 Claims, 3 Drawing Sheets

APPARATUS FOR SEPARATING PARTICLES OF COHESIVE MATERIAL ACCORDING TO SIZE AND PROCESS

BACKGROUND OF THE INVENTION

1. Field of the Invention

The present invention provides a milling/sizing apparatus which includes individual and/or nested sieves each of which may also include a quantity of beads, disks and/or other geometric or non-geometric shapes. The sieves can be rotated, vibrated or agitated in any and all combinations by various methods to achieve independently horizontal rotation and vertical reciprocation (similar to a merry-go-round) to efficiently segregate, size or mill cohesive powder particles to specific size ranges. The invention also contemplates use of the apparatus in the sizing and quantification of aggregated particles of cohesive aggregates in general, such as ores, animal and human foodstuffs, fossil fuels, and the like.

2. Statement of the Related Art

Classification of powder particle size, and milling to a specific size range(s) has become of increasing importance in mining, agriculture, energy production, and the like. By way of example there can be mentioned size classification of sulfur, coal, inorganic and organic pigments, grains, starches, sugars, and the like. Attention to particle size is especially critical in the pharmaceutical field (and related fields) due to the increased need to control drug delivery rates. The control of particle size of hydrophobic drug substances has become of major importance in the formulation of solid oral dosage forms (e.g., tablets, capsules), liquids (e.g., suspensions, transdermal), and semisolids (e.g., creams, ointments, lotions, and the like). A substantial need exists for apparatus and method which can separate and/or mill all such materials, and especially cohesive particulate drugs, into the specifically required size ranges better than systems known in the art.

With respect to the present state of the art, Remington's Pharmaceutical Sciences, Easton, Pa., Mack Publishing Company, 18th Edition, page 1617, 1618 and 1620, 1990, notes that commercially available apparatus provide centrifugal impact mills. By means of a rotor, material is milled and pushed through a sieve or screen. As examples, Remington cites the "QUICK SIEVE" (Glatt Air), the "TURBOSIEVE" and the "CO MILL." Also mentioned in Remington are mechanical sifters such as the "GYRO-WHIP" (Sprout-Waldron). It is believed that in none of the foregoing are used multiple sieves with the ability to operate by moving the sieve surface(s) in a horizontally rotating pattern superimposed on a vertically reciprocating pattern and effect segregation milling, i.e., they do not operate like a merry-go-round.

Other prior art apparatus are described in Perry, Chemical Engineers' Handbook, New York, McGraw-Hill Book Company, 5th Ed., pages 21–44 and 21–45, 1973, which illustrates sieves and shakers such as the "RO-TAP" of the W. S. Tyler Company, the "END-SHAK" of Newark Wire Cloth Company, the "DYNAMIC" of SoilTest, Inc., and the "CENCO-MEINSER" of Central Scientific Company. It is believed that in none of the foregoing are used multiple sieves with the ability to operate by moving the sieve surface(s) in a horizontally rotating pattern superimposed on a vertically reciprocating pattern. The use of objects to facilitate the process is not mentioned.

Most of the patent literature related to reciprocating sieve shaker apparatus describes mechanisms for vertically shaking stacks of sieves. Reference is made in this connection to Smith et al, U.S. Pat. No. 3,744,631; Tonjes et al, U.S. Pat. No. 2,959,285; Gundlach, U.S. Pat. No. 4,233,151; Gilson, U.S. Pat. No. 2,358,453. Such devices do not provide for horizontal rotation of the screen stack and they are silent on the possibility of using milling aids to minimize plugging of the sieve openings, reducing agglomerated particles of cohesive substances, and milling powders to any desired size range.

It has now been discovered and is the subject matter of the present invention that if sieves or stacks of sieves are adapted to rotate horizontally and at the same time agitated vertically, cohesive particles are efficiently sized and deagglomerated, especially if the individual sieves are loaded with effective amounts of shaped three-dimensional milling aids.

SUMMARY OF THE INVENTION

The present invention provides an efficient milling device and process which is unique in that it combines milling and sieving to specific size ranges and can provide both qualitative and quantitative particle information. In contrast to sieving alone by vertical reciprocation, cohesive materials can be efficiently sized and segregated using the present invention.

In accordance with one aspect of the invention, there is provided an apparatus for separating particles of a cohesive material according to size comprising A. a main stationary frame structure;

B. a drive means mounted inside a tilting base and a motor on the frame; and

C. a generally vertically cylindrical screening unit, the bottom of which is supported on the said main frame and being adapted for independent horizontal rotation and vertical reciprocation by said drive means, said screening unit comprising upper and lower sub-frame members, at least one removable screening tray, one tray spacer member for each screening tray in the unit, and tray clamping means for the unit.

In preferred embodiments the screening unit also includes an effective amount of means for facilitating milling, sieving and/or deaggregation of the particles of cohesive material, and those wherein such means for milling comprise inert three-dimensional solid, hollow, porous, non-porous, and the like, shapes. In other preferred features the invention contemplates apparatus as defined above wherein the screening unit comprises a plurality of screening trays and the screening trays and the spacer members are stacked alternately and clamped between the upper and lower sub-frame members.

In another major aspect, the present invention contemplates a method comprising separating particles of a cohesive form of a polydisperse compound or composition, according to size, said method comprising milling and sizing the compound or composition in an apparatus as defined above until the separation according to size is substantially complete and recovering the separated particles. For example, the compound or composition fed to the process can comprise an ore, an animal or human foodstuff, a fossil fuel, or a pigment.

In preferred embodiments of the method aspect of the invention, the compound or composition will comprise a polydisperse form of a powder comprising at least one pharmaceutically-active compound, alone, or in further combination with at least one pharmaceutically-acceptable necessity. Special mention is made of the method wherein the pharmaceutically-active compound will comprise the antiviral drug nevirapine, particularly nevirapine hemihydrate; in a another preferred embodiment of the present invention, the pharmaceutically-active compound will comprise the antiarrhythmic drug mexiletine, especially mexiletine hydrocloride.

BRIEF DESCRIPTION OF THE DRAWINGS

The drawings of this invention comprise.

DETAILED DESCRIPTION OF THE INVENTION

Figure 1:
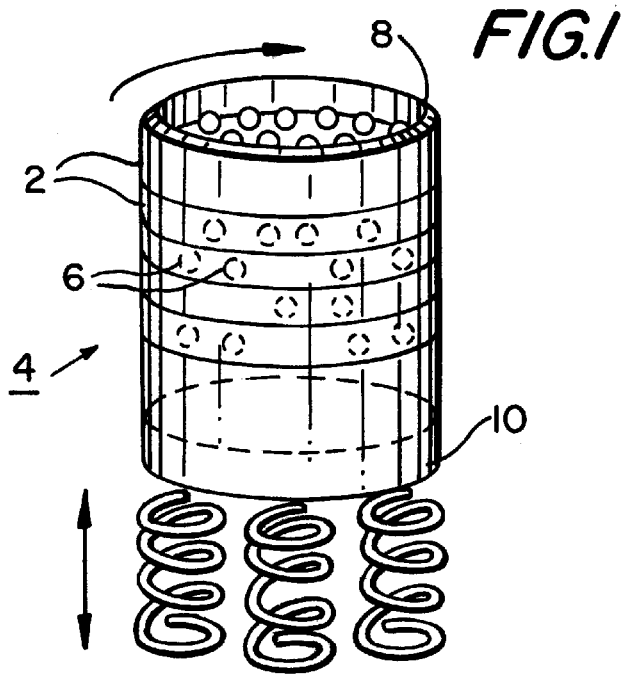
FIG. 1 which is a schematic perspective view of a stack of screens of the invention showing by arrows the direction of horizontal rotary motion superimposed on a vertical reciprocating motion and embodies a preferred form of the invention by including milling objects in the spacers above each screen in the series.
Figure 3:
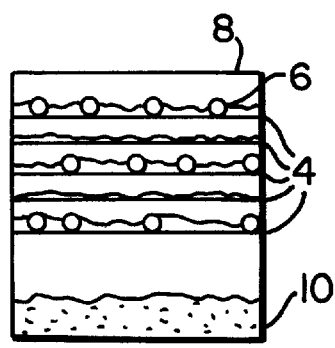
FIG. 3 is a vertical sectional view of the stacked sieves of FIG. 1 in which the sieve opening sizes are changed, i.e., either increased or reduced from top to bottom showing how the apparatus of the present invention can produce particles of specific size ranges.

Referring to FIG. 1, to effect particle sizing with multiple sieves, material may be placed on the most coarse sieve 2 in a stack of sieves 4 with the coarsest sieve being, for example, on the top of the stack. Into each sieve or into selected sieves a quantity of objects 6, such as beads, disks, or the like, may be introduced and the stack of sieves 4 is agitated by a means (not shown) which provide motions somewhat similar to a merry-go-round, as is shown by the arrows in FIG. 1. For manual operation, after equilibrium is reached, the stack is separated into separate sieves and the various particles are recovered. Merely by way of illustration, and referring to FIG. 3, five sieves 4 having from top to bottom respective openings of 1000 μm, 500 μm, 250 μm, 125 μm and 63 μm are stacked below an upper sub-frame member 8 comprising an 18 mesh sieve having 1 mm openings and above a lower sub-frame member 10 for collecting fines passing through the lower most screen. It is also possible, as mentioned above, to vary the order of opening sizes going from top to bottom. The operation is continued until the desired quantity of material is obtained and the sieve fractions are collected and the relative size is determined by the mesh openings in the respective sieves. For example, the collected particles will have sizes <1000 μm and >500 μm; <250 μm and >125 μm, and the collected fines in sub-frame member 10 will all be <63 μm.

Figure 2:
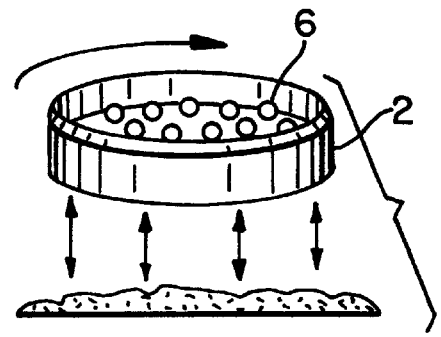
FIG. 2 shows an embodiment of the present invention which is a schematic perspective view of a single screen again showing by arrows the direction of horizontal rotary motion superimposed of a vertical reciprocating motion and embodies a preferred form of the invention by including milling objects in the spacer above the screen.

Particle sizing and quantification with a single sieve in accordance with the present invention can be carried out in an apparatus shown schematically in FIG. 2. The powder feed may be placed on sieve 2 and a quantity of objects 6, beads, disks or the like, is placed on the powder loaded sieve, which, for example, will have openings of 1 mm (an 18 mesh sieve). Agitation in the indicated directions is next carried out until the amount of desired material is milled through the sieve openings, collected in pan 10 and all of the collected particles will be of less than 1 mm in size.

In those instances wherein attrition due to milling may be a shortcoming, some cohesive materials can be classified without difficulty or departing from the invention by using the apparatus of FIGS. 1 and 2, but omitting the use of objects 6 or by selecting objects which due to their process optimization do not mill or do not selectively mill.

Figure 4:
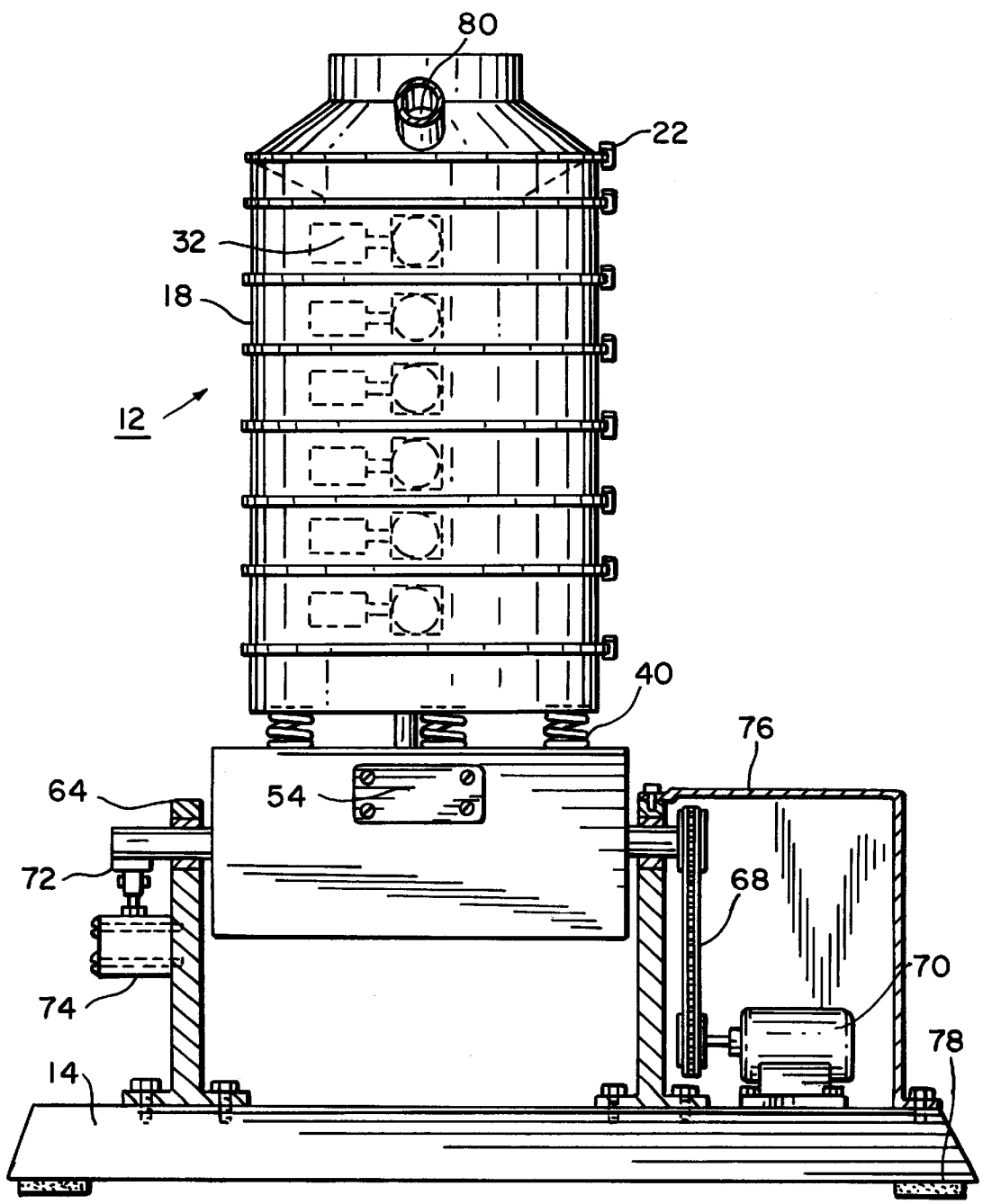
FIG. 4 is a front view of an apparatus which is a preferred form of the present invention showing a stationary base, a motor driven horizontally rotatable stack of screens and a solenoid-actuated array of springs to induce vertical motion to the stack of sieves and including a feed inlet and individual sieve outlets for continuous in-line operation to classify and separate cohesive powders.
Figure 5:
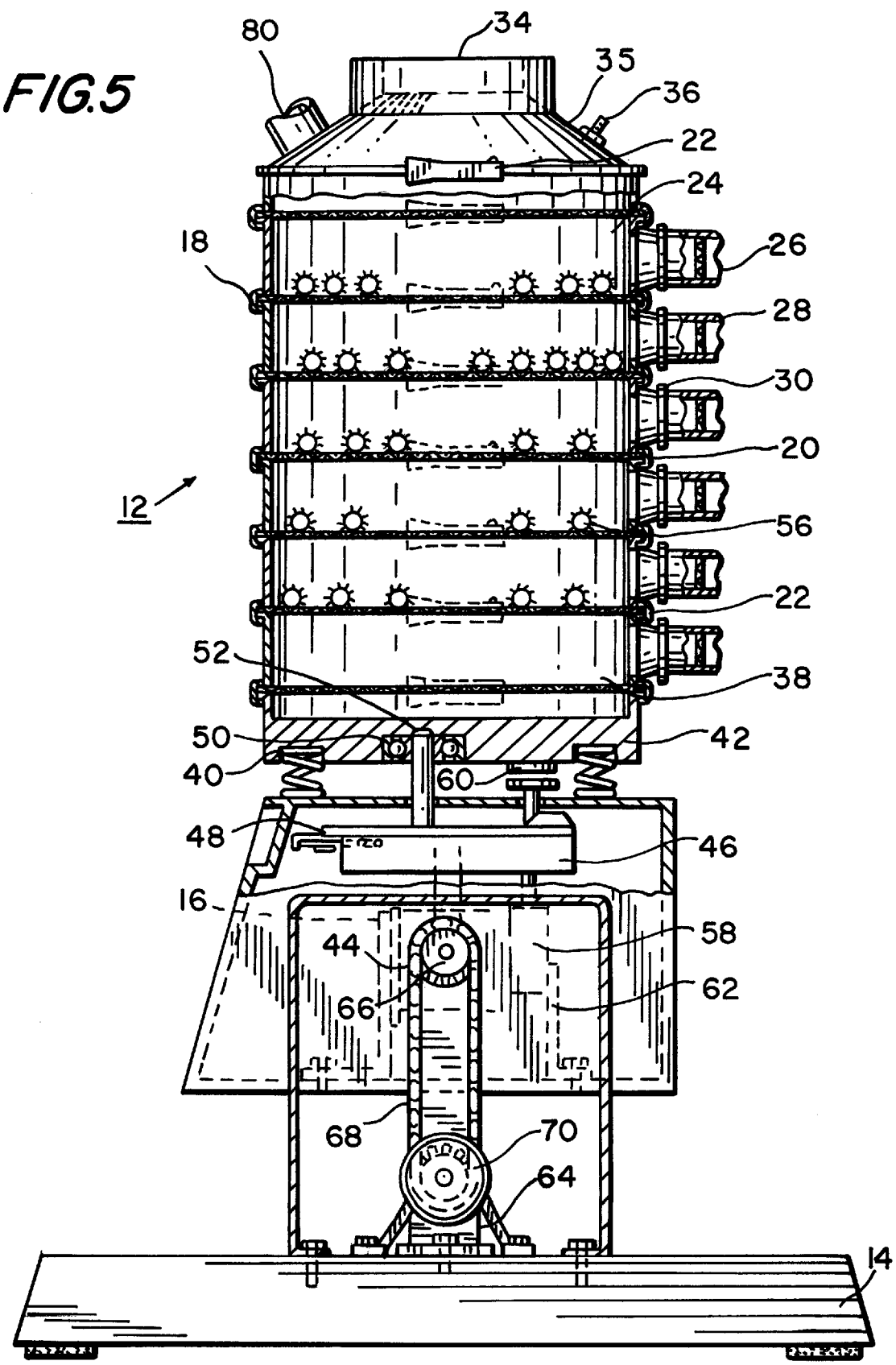
FIG. 5 is a side cross-sectional view of the apparatus of FIG. 4, showing particularly the sieve outlets, the motor-driven rotation disk with counterweight, the pulse solenoid used to induce vertical vibratory motion to the spring-loaded stack of screens and a motor-driven tilting drive to facilitate intermittent removal of the classified products.

FIGS. 4 and 5 show an apparatus according to the present invention which is suitable for in-line production use, as contrasted with batch operation. Referring to FIGS. 4 and 5, unit 12 comprises main stationary frame structure 14, a drive means 44 mounted inside a tilting base (details shown in FIG. 5) and a generally vertically cylindrical screening unit 18, the bottom of which is supported on the main frame. Referring to FIG. 5, screening unit 18 is constructed as a stack comprised of a series of sieves (screens) 20 held in place with large quick release clamps 22. Coupled to each sieve are stack spacers 24 with outlets 26, outlet retaining screens 28 gates 30, and stack outlet gate solenoids 32 (shown in phantom in FIG. 4). A source of sonic agitation 34 can be located in the upper sub-frame member 35 at the top of the stack along with a powder level sensor 36, which has capability to automatically run a feed auger (not shown). Lower sub-frame member 38 located at the bottom of the stack comprises a pan to collect materials passing through the other sieves (fines). Stack 12 is supported on six springs 40 that are retained on each end to a mechanical closure on stack base 42. The drive means comprises variable speed motor 44 mounted on the tilting base the motor being coupled to rotation disk with counterweight 46 and adjustable slide shaft 48 for providing eccentric motion. A shaft with pressed roller bearing 50 is in the stack base to facilitate rotation. To the associated shaft 52 is attached the eccentric with a retaining clip. Door 54 (FIG. 4) in the front of the mechanical closure provides access to the eccentric slide for adjustment to permit the intensity of the shaking motion to be varied. The support springs allow the stack to rotate horizontally and vertically with a shaking motion. The screens combined with their respective spacers are designed to accept objects 56 for facilitating the milling/sieving or deaggregation process. Such objects may be spherical or geometric or essentially any shape which suits the specific process needs. To assist in the up-and-down vertical motion, pulsing solenoid 58 and rapping plate 60 are attached respectively to the bottom frame through bracket 62 and to the stack base. This is adapted to produce a "rapping/tapping" action. For production use, the stack is adapted to pivot via a welded shaft between two stanchions 64, which are bolted to base plate 14. Tilt sprocket 66 is attached to one end of the pivoting shaft and coupled with roller chain 68 to reversible tilting motor 70 with an associated sprocket. As is more clearly seen in FIG. 4, the non-driven side of the tilting shaft has a "lobe" 72 which actuates electrical switch 74. During tilting, switch 74 opens the sieve outlet gate solenoids 32, allowing screened/milled powders to exit without the need to break down the screening unit. At the same time, the switch also shuts off the auger feed. When the stack returns to the upright mode, the solenoid gates close and the feed auger returns to the preset run mode. The control of tilting may be set manually or automatically (based on a cycle). Guard cover 76 (FIG. 4) covers the tilt motor and chain. Rubber feet 78 isolate the machine from moving due to vibration. Of course, construction materials needed for the apparatus may be varied consistent with the intended purpose and individual needs without departing from the spirit or scope of the present invention.

When used herein and in the appended claims, the term particles of cohesive materials refers in its broadest sense to powders recovered by mining, such as ores, e. g., iron ore, copper ore, limestone, fossil fuels, such as coal, coke, and the like, sulfur, cement, agricultural fertilizers and herbicides, animal feedstuffs, based on grains, human feedstuffs such as cereals, corn starch, sugars, pigments for paints, such as titanium dioxide, fillers for plastics, such as talc, silica, and the like, either as dug, manufactured or harvested, and even if subjected to prior treatment such as ball milling, hammer milling, jet milling and the like. The term pharmaceutically-active compound refers to known drugs, and their pharmaceutically acceptable addition compounds, such as acid- and base-addition salts, as well as hydrated forms, and the like. The term pharmaceutically-acceptable necessities is used in the art-recognized sense to embrace substances which are of little or no therapeutic value, but which are useful in the manufacture and compounding of various pharmaceutical preparations. The substances falling within this term include, without limitations, general excipients, including antioxidants and preservatives; coloring, flavoring and diluting agents; emulsifying agents and suspending agents; ointment bases; pharmaceutical solvents and miscellaneous agents, and the like. They are exemplified in Remington, cited above, Chapter 66, and hereinafter in connection with nevirapine and mexiletine.

In carrying out the process of the present invention continuously, and using an apparatus shown in FIGS. 4 and 5, material, such as the cohesive powder containing the pharmaceutically-active compound known as nevirapine monohydrate (see, e.g., Schneider et al, U.S. Pat. No. 5,569,760), is fed into stack feed inlet 80 via an auger (not shown). The auger may be run in the manual or automatic mode. In the automatic mode a powder level sensor turns the feed auger on and off based on the powder level in the upper stack. The objects to be put onto the screens with the powders are selected. With agitation (mechanical/rotatory, sonic, pulsing) the objects mill or facilitate segregation of powders either into the next screen or final pan. At a selected time the contents of the sieves are transferred, via tubing to a series of collection bins (not shown). This is accomplished by tilting the stack, which initiates the solenoids to open the outlet gates permitting the powder to flow into the tubing and hence into the collection bins. The sieve objects are retained inside the sieves by the use of screens or plates with openings smaller than the objects. The unit continues to operate with agitation in the tilt position to facilitate emptying and the feed auger is automatically shut off. The stack is held in the "empty" position based on a preset tilt hold timer. After tilting and emptying, the stack returns to the vertical position as the motor reverses itself and the solenoid gates close. The feed auger resumes operations as preset. Auto tilt can also be selected based on a cycle, performing "tilt on", "tilt hold", and "tilt off".

If the procedure is repeated, but substituting as the feed a cohesive powder containing the pharmaceutically-active compound known as mexiletine hydrochloride (see, e.g., Koppe et al, U.S. Pat. No. 3,659,019), substantially the same results will be obtained.

Pharmaceutical necessities often used with nevirapine hemihydrate include microcrystalline cellulose, lactose monohydrate, povidone, sodium starch glycolate, colloidal silicon dioxide, magnesium stearate, and the like. Pharmaceutical necessities often used with mexiletine hydrochloride include colloidal silicon dioxide, corn starch, magnesium stearate, titanium dioxide, gelatin, approved dyes, and one or more of sodium lauryl sulfate, sodium propionate, edetate calcium disodium, benzyl alcohol, carboxymethylcellulose sodium, glycerin, butylparaben, propylparaben, methyl paraben, pharmaceutical glaze, ethylene glycol monoethyl ether, soya lecithin, dimethylpolysiloxane, refined shellac (food grade) and other inactive ingredients.

The above-mentioned patents and publications are incorporated herein by reference.

While there is described above the principles of this invention in connection with specific apparatus and a two cohesive powders, it is to be clearly understood that this description is made only by way of example, and not as a limitation to the scope of this invention. For example as feeds to be milled and/or classified, there can be substituted polydisperse forms of compounds such as sulfur, bituminous coal dust, soft talc, barium sulfate, titanium dioxide, pelletized animal feed, corn starch, sucrose, graphite, limestone, and the like. All such variations are within the full intended scope of the appended claims.

I claim:

1. An apparatus for separating particles of a cohesive material according to size comprising A. a main stationary frame structure;

B. a drive means mounted inside a tilting base and a stationary motor on the frame; and C. a generally vertically cylindrical screening unit, the bottom of which is supported on the said main frame and being adapted for independent horizontal rotation and vertical reciprocation by said drive means, said screening unit comprising upper and lower sub-frame members, at least one removable screening tray, one tray spacer member for each screening tray in the unit, and tray clamping means for the unit.

2. An apparatus as defined in claim 1 wherein said screening unit also includes an effective amount of means for facilitating milling, sieving and/or deaggregation of the particles of cohesive material.

3. An apparatus as defined in claim 2 wherein said means comprise inert three-dimensional shapes.

4. An apparatus as defined in claim 1 wherein said screening unit comprises a plurality of said screening trays and the screening trays and the spacer members are stacked alternately between the upper and lower sub-frame members.

* * * * *